United States Patent
Ruddle et al.

(10) Patent No.: US 6,917,883 B1
(45) Date of Patent: Jul. 12, 2005

(54) EFFICIENT CIS-ELEMENT DISCOVERY METHOD USING MULTIPLE SEQUENCE COMPARISONS BASED ON EVOLUTIONARY RELATIONSHIPS

(75) Inventors: Frank H. Ruddle, New Haven, CT (US); Kenta Sumiyama, New Haven, CT (US); Chang-Bae Kim, New Haven, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 10/345,080

(22) Filed: Jan. 15, 2003

Related U.S. Application Data

(60) Provisional application No. 60/349,297, filed on Jan. 15, 2002.

(51) Int. Cl.[7] .............................................. G06F 17/00
(52) U.S. Cl. ......................................... 702/20; 702/19
(58) Field of Search ...................................... 702/19, 20

(56) References Cited

PUBLICATIONS

Becker, D., Jiang, Z., Knodler, P., Deinard, A. S., Kidd, K. K., Shashikant, C. S., Ruddle, F. H., and Schughart, K. (1996). Conserved regulatory element involved in the early onset of Hoxb6 gene expression. *Dev. Dyn.* 205: 73–81.

Bradshaw, M. S., Shashikant, C. S., Belting, H. G., Bollekens, J. A., and Ruddle, F. H. (1996). A long–range regulatory element of Hoxc8 identified by using the pClasper vector. *Proc. Natl. Acad. Sci. USA* 93: 2426–2430.

deJong, W. W. (1998). Molecules remodel the mammalian tree. *Trends Ecol. Evol.* 13: 270–275.

Gumucio, D. L., Shelton, D. A., Zhu, W., Millinoff, D., Gray, T., Bock, J. H., Slightom, J. L., and Goodman M. (1996). Evolutionary strategies for the elucidation of cis and trans factors that regulate the developmental switching programs of the beta–like globin genes. *Mol. Phylogenet. Evol.* 5: 18–32.

Saitou, N., and Nei, M. (1987). The neighbor–joining method: A new method for reconstructing phylogenetic trees. *Mol. Biol. Evol.* 4: 406–425.

Shashikant, C. S., Bieberich, C. J., Belting, H. G., Wang, J. C., Borbely, M. A., and Ruddle, F. H. (1995). Regulation of Hoxc–8 during mouse embryonic development: Identification and characterization of critical elements involved in early neural tube expression. *Development* 121: 4339–4347.

Shashikant, C. S., Kim, C. B., Borbely, M., Wang, W., and Ruddle, F. H. (1998). Comparative studies on mammalian Hoxc8 early enhancer sequence reveal a baleen whale–specific deletion of a cis–acting element. *Proc. Natl. Acad. Sci. USA* 95: 15446–15451.

Shashikant, C. S., and Ruddle, F. H. (1996). Combinations of closely situated cis–acting elements determine tissue–specific patterns and anterior extent of early Hoxc8 expression. *Proc. Natl. Acad. Sci. USA* 93: 12364–12369.

Raught, B., Liao, W. S.–L., and Rosen, J. M., (1995). Developmentally and hormonally regulated CCAAT/enhancer–binding protein isoforms influence □–casein gene expression. *Mol. Endocrinol.* 9: 1223–1233.

*Primary Examiner*—James Martinell
(74) *Attorney, Agent, or Firm*—Fish & Neave IP Group, Ropes & Gray LLP

(57) ABSTRACT

A method is described for efficiently searching non-coding DNA for known control elements. Short conserved DNA sequences can be identified among 3 or more species by selecting DNA sequences from species having a total genetic distance larger than one substitution per site at a neutrally evolving region and calculating the total substitutions using pair-wise genetic distances, with the pairs for comparison selected based on phylogenetic relationships.

18 Claims, 2 Drawing Sheets

EFFICIENT CIS-ELEMENT DISCOVERY METHOD USING MULTIPLE SEQUENCE COMPARISONS BASED ON EVOLUTIONARY RELATIONSHIPS

CROSS-REFERENCE TO OTHER PATENT APPLICATIONS

This application claims the benefit of U.S. provisional Application No. 60/349,297 filed Jan. 15, 2002, the subject matter of which is incorporated herein by reference in its entirety.

GOVERNMENT GRANTS

This work was made with Government support under Grant GM-09966 awarded by the National Institute of Health and Grant IBN-9630567 awarded by the National Science Foundation. Therefore, the U.S. Government has certain rights in this invention.

BACKGROUND OF THE INVENTION

The discovery of cis-elements or control elements in non-coding DNA poses a difficult problem in genome analysis. Functional analysis by means of reporter constructs expressed in transgenic organisms is the most reliable method, but is by itself time-consuming and expensive. Searching non-coding DNA for known control elements by sequence analysis is problematic, since protein binding motifs are short, in the range of 8–10 base pairs (bp), and occur frequently by chance. Heretofore, the most reliable sequence analysis method has been the comparison of homologous sequence domains in related but moderately evolutionarily divergent species such as, for example, mouse and human. In such pair-wise combinations, control elements are conserved because they serve a vital function and can be identified by their similar sequences. Single pair-wise comparisons, however, allow the discovery of conserved sequence strings only at low resolution and without specific identity.

Functional analysis is a time-consuming and expensive approach to genomic analysis and a more efficient, rapid method of identifying genomic areas of interest would be beneficial.

SUMMARY OF THE INVENTION

The present invention relates to a method of applying multiple evolutionarily related sequence comparisons to genomic sequences to identify short conserved DNA sequences, such as control elements (e.g., promoters, enhancers, and silencers). In one embodiment, the short conserved sequences or motifs are identified through comparisons of genomic DNA sequences from at least 3 related species. In specific embodiments, genomic sequences from 4 to 8 (e.g., 4, 5, 6, 7 or 8) related species are compared, as described herein, to identify control elements. Sequences or motifs thus identified to be control elements can be further assessed, to confirm their function, using known functional analysis techniques.

The invention is directed to a method for genome analysis, and more particularly to a method for efficiently searching noncoding DNA for known control elements. The method according to one embodiment of the invention is directed to applying multiple evolutionarily related sequence comparisons to identify protein binding cis-element motifs. The method of the present invention enables identification of short conserved genoric sequences which are, for example, control elements, without the need for the widely-used and cumbersome functional analysis techniques, which can be used to confirm the role of sequences identified.

According to one aspect of the invention, at least one short conserved DNA sequence is identified among 3 or more species by selecting DNA sequences from species having a total genetic distance larger than one substitution per site at a neutrally evolving region, and calculating the total substitutions using pair-wise genetic distances, with the pairs for comparison selected based on phylogenetic relationships.

According to another aspect of the invention, putative protein binding sites are predicted by identifying short, homologous DNA sequences from among 3 or more species having a total genetic distance larger than one substitution per site at a neutrally evolving region, and calculating the total substitutions using pair-wise genetic distances, with the pairs for comparison selected based on phylogenetic relationships. A protein binding site is indicated by a number of substitutions in the short sequences that is less than a predetermined number for a given length of the short sequences.

According to yet another aspect of the invention, a computer readable medium has stored thereon instructions for choosing DNA sequences from among three or more species having a selected genetic distance at a neutrally evolving region, defining a window having a width capable of identifying a short conserved DNA sequence, calculating a total number of substitutions within the window using pair-wise genetic distances, with the pairs for comparison selected based on phylogenetic relationships, and indicating a non-coding sequence motif by the number of substitutions in the short sequences being less than a predetermined number for a given length of the short sequences.

Embodiments of the invention may include one or more of the following features. The substitutions can be calculated using the formula $$D_{total} = 1/2 \left[ \sum_{i=1}^{n-1} (D_{i,j+1}) + D_{n,1} \right]$$

where $D_{i,i+1}$ is a pair-wise p-distance between species i and i+1, and n is the number of species used. Conserved sequences are referred to as short if they are about 6 to 12 base pairs in length. The ensuing high resolution of the method enables identification of putative transcription factor binding sites. The term "transcription factor" herein refers to any protein whose presence or absence contributes to the initiation of transcription but which is not itself a part of the polymerase. Transcription factors may either stimulate or repress transcription. Some transcription factors contain a DNA binding domain, which is that part of the transcription factor which directly interacts with the expression control element of the target gene.

The short conserved DNA sequences can be identical or similar, with up to three base substitutions permitted in a 10 base pair window.

The method is particularly effective if more than three closely related species are compared. The DNA sequence can be located upstream, downstream, or within gene encoding regions. The short, conserved DNA sequence identified can be a control element and the control element can be further assessed by a fimctional analysis technique.

Further features and advantages of the present invention will be apparent from the following description of preferred embodiments and from the claims.

BRIEF DESCRIPTION OF THE DRAWINGS

The following figures depict certain illustrative embodiments of the invention. These depicted embodiments are to be understood as illustrative of the invention and not as limiting in any way.

DETAILED DESCRIPTION OF CERTAIN EMBODIMENTS

The invention is directed to a method for genome analysis, and more particularly to a method for efficiently searching non-coding DNA for known control elements. As used herein, the terms "control element," "control motif," "cis-element," and "short conserved DNA sequence" are used interchangeably, referring to DNA sequences, such as initiation signals, enhancers, promoters and silencers, which induce or control transcription of DNA sequences with which they are operably linked. Control elements of a gene may be located in introns, exons, coding regions, and 3' flanking sequences. Some control elements are "tissue specific," i.e., affect expression of the selected DNA sequence preferentially in specific cells, while others are active in many or most cell types. Such control elements can serve as binding sequences for proteins such as transcription factors.

In certain embodiments, the method of the present invention can be used to efficiently identify short conserved DNA sequences based on multiple sequence comparisons of at least 3 related species. In particular, the method described herein can be used to identify short (~6 bp) sequence strings.

Evolutionary relationships can be used to discover control elements such as enhancers and promoters in genomic DNA sequences in proximity to the coding elements of genes. It has been shown that control elements between related but moderately divergent species are frequently similar, presumably to conserve a vital function. Human and mouse provide a good example, having a common ancestor extant some one hundred million years ago. Exemplary comparisons between noncoding sequences of human and mouse Hoxc8 and Hoxc6 genes have revealed sequence elements that are highly conserved. Subsequent functional analysis has confirmed these elements as enhancers. Although comparisons between two species can be useful, the identification of protein binding sites is difficult because of their small footprint of typically between 8 and 10 bp.

The control element discovery can be dramatically improved by using multiple sequence comparisons based on phylogenetic relationships among multiple species sharing a common evolutionary development or history. Certain regions in the DNA (phylogenetic footprints) have remained unchanged during the evolutionary process, resulting in non-coding sequence motifs that show 100% conservation in several species over a region of six or more contiguous base pairs.

One way of using multiple sequences is to calculate all possible pair-wise comparisons and taking an average. However, this method is problematic, since it yields a biased estimation of substitutions that occurred in ancestral branches. This error can be eliminated or at least substantially reduced by estimating total substitution numbers on a phylogenetic tree by using specific combinations of pair-wise distances.

Figure 1:
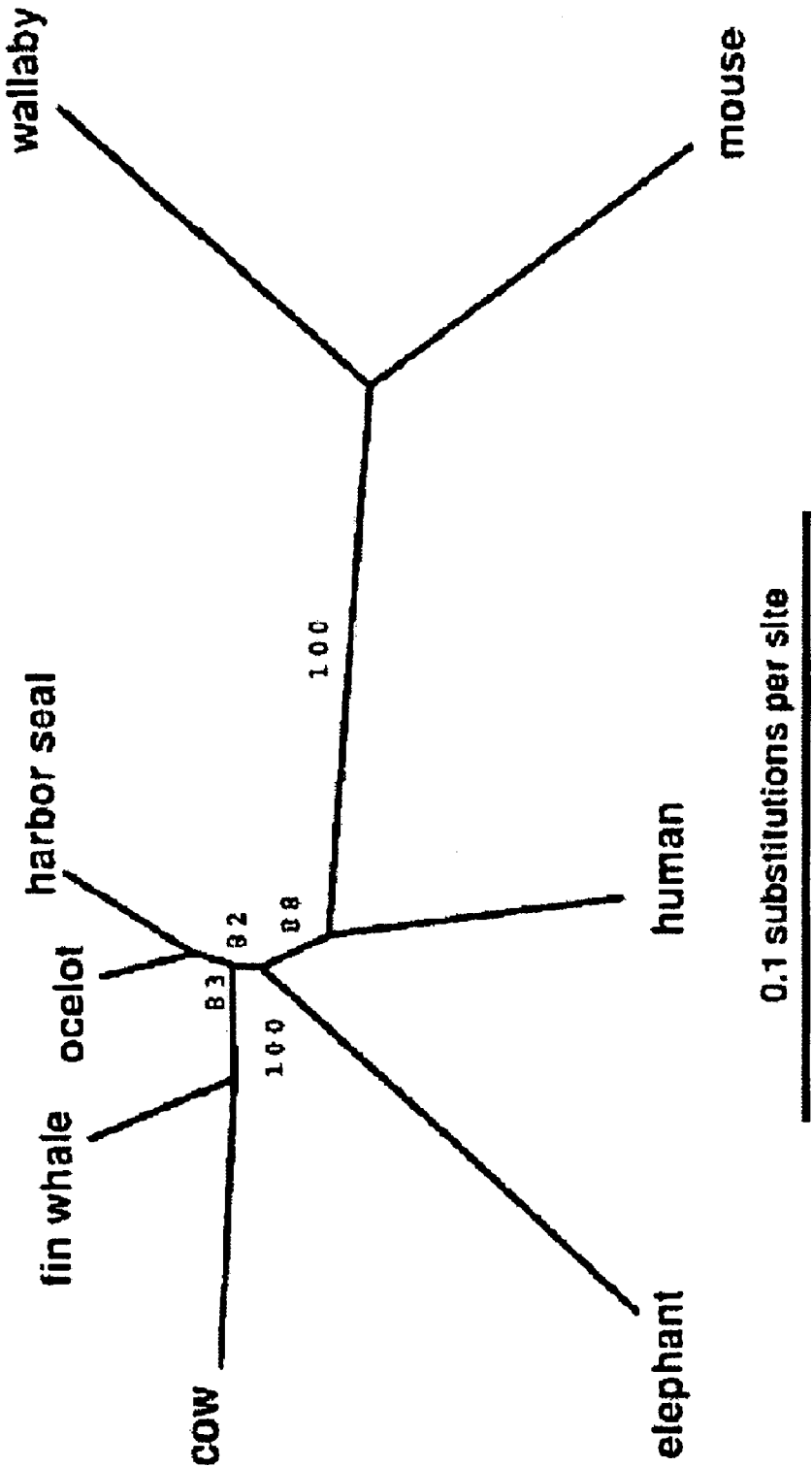
FIG. 1 depicts a neighbor-joining tree among eight mammalian species.

Referring now to FIG. 1, eight mammalian species (human, mouse, wallby, harbor seal, ocelot, fin whale, cow, and elephant) were selected for constructing a phylogenetic tree consistent with established specific relationships using a neighbor joining (NJ) method. The construction of phylogenetic trees is described by N. Saitou and M. Nei (Mol. Biol. Evol. 4(4): 406–425, 1987), the entire content of which is incorporated herein by reference. In a neighbor-joining tree, the elements of the tree (species) are connected through a single interior node in an unrooted, bifurcated tree. A distance or branch length $D_{i,i+1}$ is defined between neighbors, with $D_{i,i+1}$ representing, for example, a degree of relationship between neighboring elements of the tree, such as the number of nucleotide substitutions per site. The construction of a NJ tree typically starts with a star-like tree, and the sum of the branch lengths are minimized, which is akin to a least-squares estimate. The numerical values on the branches of the NJ tree of FIG. 1 are bootstrap probabilities out of 1000 replications, i.e., there is a substantially 100% probability for conservation of the murine enhancer between human, mouse and wallaby, but only a 72% probablility between harbor seal and human.

It is noteworthy that a NJ tree may not always represent minimum evolution tree, which also may not necessarily be the true tree.

The described method is applied to a known enhancer, such as the murine early enhancer of Hoxc8, using a small-window analysis and calculating the total number of substitutions on the tree in each window with the calculation of statistical significance. The position and characteristics of the Hoxc8 enhancer is calculated using the eight aforementioned species of mammals, and these results are compared with those obtained by the more common two-species (mouse/human) comparison. The tree topology yields a non-redundant estimate of total substitutions per site ($D_{total}$) by the simple equation $$D_{total} = 1/2 \left[ \sum_{i=1}^{n-1} (D_{i,j+1}) + D_{n,1} \right],$$

where $D_{i,i+1}$ is a pair-wise p distance between species i and i+1, and n is the number of species used. As mentioned above, specific combinations of pair-wise distances for obtaining the non-redundant approximate total substitution numbers are selected based on the phylogenetic relatedness between the species. In the exemplary process, Species-one human) is selected as the starting point select, Species-two (mouse) as its neighbor on the phylogenetic tree, and so forth, until returning to the starting point. The pair-wise distances $D_{human, mouse}$, $D_{mouse, wallaby}$, $D_{wallaby, harbor-seal}$, and so on, are then summed in the equation. Other series can be calculated if compatible with tree topology. Those procedures are simple, so that all calculations and plot drawing can be performed by using a conventional computer program, such as Microsoft® Excel®.

Figure 2:
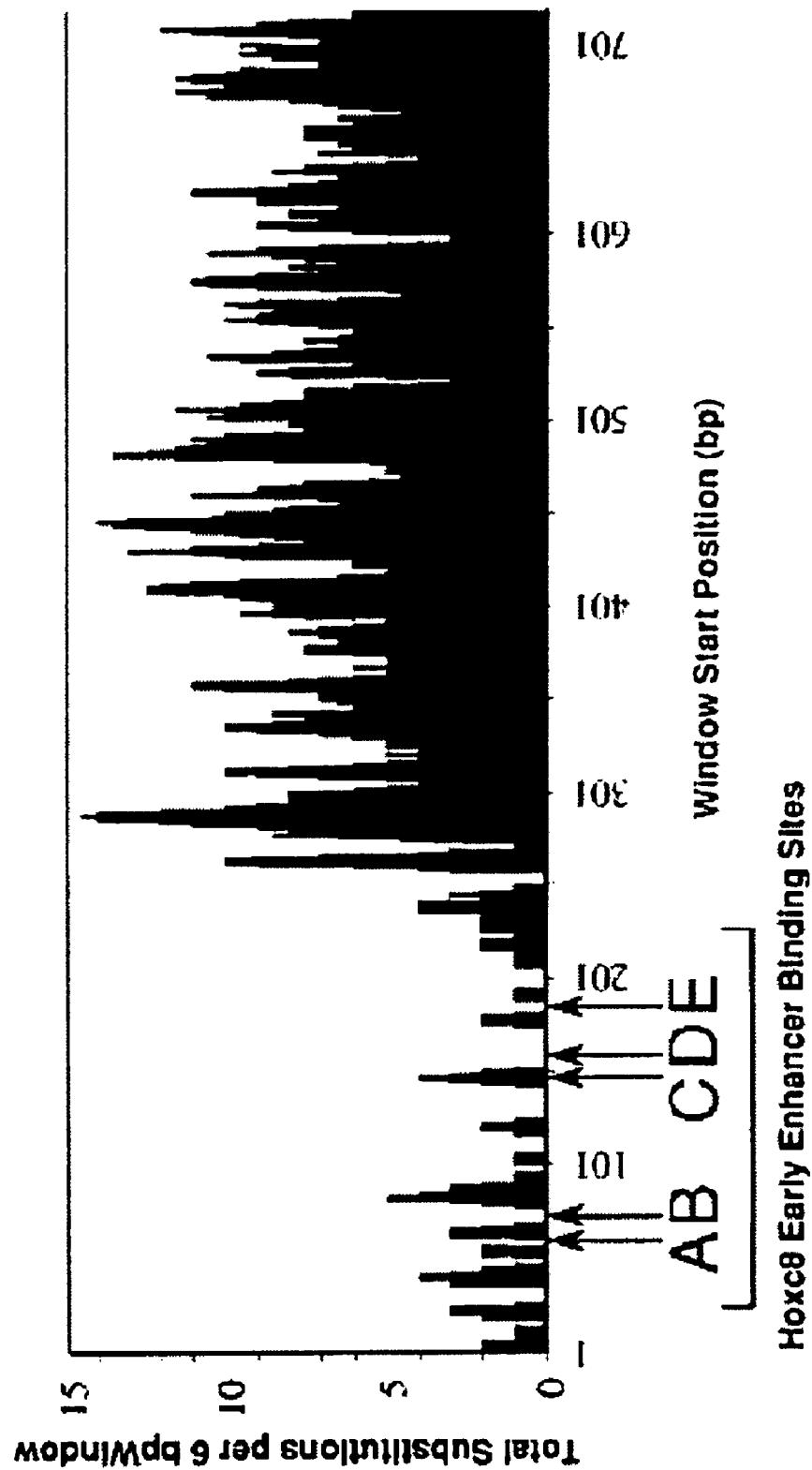
FIG. 2 depicts an evolutionary conservation plot of the Hoxc8 early enhancer region using the phylogenetic relationship of FIG. 1; horizontal axis: first nucleotide position of each window; vertical axis: accumulated nucleotide substitutions on the tree. Arrows indicate positions for known transcription factor binding sites, A, B, C, D, and E.

Referring now to FIG. 2, the aforedescribed method is applied to a sliding window analysis using a window size of 6 bases. FIG. 2 shows an evolutionary conservation plot of Hoxc8 early enhancer region using the eight mammalian sequences and the phylogenetic relationship of FIG. 1. The horizontal axis indicates first nucleotide position of each window. The vertical axis indicates accumulated nucleotide substitutions on the tree. The arrows A, B, C, D, and E indicate positions for known transcription factor binding sites. Other gaps in the early enhancer (zero substitutions) may indicate other, thus far unidentified binding sites. Sequences for the eight mammalian species were obtained by PCR using highly conserved sequences just 5' to the enhancer region and some 400 bases downstream from its 3' limit.

As seen clearly from FIG. 2, the early enhancer is clearly distinguished over its entire domain extending from bp 1 to 250. The region between about bp 250 to above 700 can be considered as a neutral evolving region, with little discernible base pair conservation between the considered species. Previously determined known protein binding sites, indicated by A, B, D, and E, are clearly distinguishable as having no substitutions. Conversely, binding site C shows four substitutions, because of the inclusion of the fin whale, a member of the baleen clade of whales, all of which have a 4-bp deletion of the C element. If the baleen whale is excluded from the analysis, element C is identified also as a perfectly conserved motif along with A, B, D, and E. It has been independently confirmed that the binding site C is representative of the sternum which is absent in the baleen whale. Thus, the multiple comparison method has the capability of detecting polymorphism in enhancer binding sites. This can be achieved by calculating nonredundant substitutions among species. The multiple comparison method is capable of predicting putative protein binding sites, such as multiple invariant sites not designated by a letter in FIG. 2. One of these sites is palindromic, suggestive of a functional protein binding site, which can be confirmed with a functional assay.

The exemplary method of the invention is based on determining the number of substitutions on the tree within a certain size of window; accordingly, the method can also be applied to other multiple sequences if their multiple alignment is reliable. A larger total number of substitutions is favorable for better reliability. However, if too distantly related species are used, multiple alignment among them may not be reliable because of genomic rearrangement, which is frequently observed among distantly related species. It is therefore advantageous to use for the calculation a larger number of relatively close species (such as the eight representative mammalian species) that have relatively smaller pair-wise distances.

Table 1 below shows a comparison of the probability for 100% conservation between simple pair-wise comparison and multiple eight-species sequence comparison based on the phylogenetic relationship of FIG. 1 for various window sizes. A large value for the probability translates into a low confidence that changes under these conditions can be observed. The probability values in Table 1 demonstrate the advantage of an eight-species comparison over a two-species comparison. Exact probabilities of 100% conservation within several window sizes show that an eight-mammalian-species comparison can achieve statistical significance of P<0.05 by 6-bp conservation, whereas a simple pair-wise comparison requires almost 20-bp conservation for the same level of significance. The sequence length of 20-bp is considerably greater than the typical size range of binding sites of approximately 6–10 nucleotides. If a 10-bp window is used, up to 3 substitutions are allowed within each window (P<0.01). The window-based method is hence capable of identifying nearly perfect conservation, without assuming perfect 6-bp core conservation. Window size can be varied according to the total number of substitutions expected under neutral conditions, which corresponds to the total distance among the exemplary species. As mentioned above, the neutral evolving part above 250 bp is also a measure of the neutral conditions. Table 1. A comparison of the probability for 100% conservation between simple pair-wise comparison and multiple eight-species sequence

TABLE 1

A comparison of the probability for 100% conservation between simple pair-wise comparison and multiple eight-species sequence

| Compared species | Window size (base pairs) | Exact probabilities of 100% conservation |
|---|---|---|
| Human-mouse pair-wise comparison | 6 | 0.31 |
| | 10 | 0.16 |
| | 20 | 0.025* |
| | 30 | 0.0037** |
| Eight-mammal comparison (human, mouse, wallaby, harbor seal, ocelot, fin whale, cow, elephant) | 6 | 0.042* |
| | 10 | 0.0018** |

*P, 0.05,
**P, 0.01.
Calculations are based on the data set of the early enhancer of Hoxc8.

In summary, the aforedescribed exemplary evolutionary multiple sequence comparison method combined with small-sized window analysis can provide a high-resolution procedure for the discovery of control elements. The method can predict the binding sites of transcription factors as well as reveal polymorphisms in control elements between clades, allowing a precise identification of control elements prior to a functional analysis, thereby saving time and resources in genome analysis.

While the invention has been disclosed in connection with the preferred embodiments shown and described in detail, various modifications and improvements thereon will become readily apparent to those skilled in the art. For example, the method can be extended to other related, moderately divergent species, such as horse, pig, bat, or to plant species. The evolutionary importance of the discovered control elements can be confirmed by functional tests, which can be done much more quickly by first identifying the location of the non-coding sequence motif. Accordingly, the spirit and scope of the present invention is to be limited only by the following claims.

What is claimed is:

1. A method for identifying at least one control element in a DNA sequence, comprising selecting DNA sequences from three or more species having a total genetic distance larger than one substitution per site at a region of the DNA sequences, and calculating the total substitutions using pair-wise genetic distances, wherein at least one control element is identified when the number of substitutions in the DNA sequences is less than a predetermined number for a given length of the DNA sequence.

2. The method according to claim 1 wherein the substitutions are calculated using the formula $$D_{total} = 1/2 \left[ \sum_{i=1}^{n-1} (D_{i,j+1}) + D_{n,1} \right],$$

where $D_{i,i+1}$ is a pair-wise p-distance between species i and i+1, and n is the number of species used.

3. The method according to claim 1 wherein the control element sequences are about 6 to 12 base pairs in length and comprise a putative transcription factor binding sites.

4. The method according to claim 1 wherein the three or more species are phylogenetically related.

5. The method according to claim 1 wherein the at least one control element is located upstream, downstream, or within gene encoding regions.

6. The method according to claim 1 wherein the control element is present in mammalian sequence.

7. The method according to claims 1 wherein the control element sequences are homologous among the three or more species.

8. The method according to claim 1 wherein the control element sequences have up to three base substitutions in a 10 base pair window.

9. The method according to claims 1 wherein the control element sequences are identical among the three or more species.

10. The method of claim 1, wherein the control element sequence identified is selected from a promoter, an enhancer, and a silencer, and the control element is further assessed by a functional analysis technique.

11. A method of identifying protein binding sites in DNA sequences, comprising
    selecting DNA sequences from among 3 or more species having a total genetic distance larger than one substitution per site at a region of the DNA sequences, and
    calculating the total substitutions using pair-wise genetic distances,
    wherein protein binding sites are identified if the number of substitutions in the DNA sequences is less than a predetermined number for a given length of the DNA sequences.

12. The method according to claim 11 wherein the substitutions are calculated using the formula $$D_{total} = 1/2 \left[ \sum_{i=1}^{n-1} (D_{i,j+1}) + D_{n,1} \right],$$

where $D_{i,i+1}$ is a pair-wise p-distance between species i and i+1, and n is the number of species used.

13. The method according to claim 11 wherein the protein binding site is a transcription factor binding sites.

14. The method according to claim 11 wherein the protein binding sites have up to three base substitutions in a 10 base pair window.

15. A computer readable medium having stored thereon instructions for i) choosing DNA sequences from among three or more species having a selected genetic distance at a region of the DNA sequences, ii) defining a window having a width capable of identifying a DNA sequence, iii) calculating a total number of substitutions within the window using pair-wise genetic distances, and iv) identifying a non-coding control element sequence by the number of substitutions in the DNA sequences being less than a predetermined number for a given length of the DNA sequences.

16. The computer readable medium of claim 15, wherein the non-coding control element sequence represents a protein binding site.

17. The computer readable medium of claim 15, wherein the three or more species have a total genetic distance larger than one substitution per site at a region of the DNA sequences.

18. The computer readable medium of claim 15, wherein the control element sequence identified is selected from a promoter, an enhancer, and a silencer, and the control element is further assessed by a functional analysis technique.

* * * * *